(12) United States Patent
Nishino

(10) Patent No.: US 7,314,598 B2
(45) Date of Patent: Jan. 1, 2008

(54) DISPENSER AND DISPENSING DEVICE

(75) Inventor: Mitsuo Nishino, Tokyo (JP)

(73) Assignees: Stack System Co., Ltd., Tokyo (JP); Juki Corporation, Tokyo (JP)

( * ) Notice: Subject to any disclaimer, the term of this patent is extended or adjusted under 35 U.S.C. 154(b) by 778 days.

(21) Appl. No.: 10/776,162

(22) Filed: Feb. 12, 2004

(65) Prior Publication Data

US 2004/0159675 A1    Aug. 19, 2004

(30) Foreign Application Priority Data

Feb. 14, 2003    (JP) ............................. 2003-036463

(51) Int. Cl.
*B01L 3/02*    (2006.01)
(52) U.S. Cl. ..................... 422/100; 73/864.11; 436/54; 436/63
(58) Field of Classification Search ................ 422/100; 73/864.11; 436/54, 63
See application file for complete search history.

(56) References Cited

U.S. PATENT DOCUMENTS 5,499,545 A * 3/1996 Kimura et al. ........... 73/864.18
2002/0051737 A1* 5/2002 Sollbohmer et al. ........ 422/100

FOREIGN PATENT DOCUMENTS

JP         6-331632         12/1994

\* cited by examiner

*Primary Examiner*—Walter D. Griffin
*Assistant Examiner*—Bobby Ramdhanie
(74) *Attorney, Agent, or Firm*—Wenderoth, Lind & Ponack, L.L.P.

(57) ABSTRACT

A dispenser has a pressure sensor enabled to detect a pressure precisely by forming a pressure sensor integrally with a syringe constructing a nozzle to thereby eliminate a pipeline or the like. The dispenser is provided for sucking and discharging a liquid from a nozzle by slidably moving a piston sliding in the inside of a syringe by a motor mounted in a body. A detection sensor for detecting the internal pressure of the inside of the syringe is integrally formed by connecting its air inlet directly to a through hole formed to extend to the inner face of the syringe.

4 Claims, 8 Drawing Sheets

DISPENSER AND DISPENSING DEVICE

BACKGROUND OF THE INVENTION

1. Field of the Invention

The present invention relates to a dispenser and a dispensing device and, more particularly, to a dispenser and a dispensing device, which are enabled to detect an internal pressure to be produced in a syringe of the dispenser, precisely and promptly by directly connecting an air intake port of a pressure sensor for detecting the pressure in the syringe, to a through hole formed through the syringe inside.

2. Related Art

As shown in FIG. 10, a dispenser 131 in the related art is internally provided with a stepping motor 152 to be activated when fed with a driving pulse signal, so that it sucks and discharges a liquid from a pipette nozzle 132. The dispenser 131 is substantially constructed to include: the pipette nozzle 132; a disposable tip 133 retained in removable engagement on the leading end of the pipette nozzle 132; a pressure sensor 134 arranged in a pressure detecting passage 180 for detecting the pressure in the pipette nozzle 132; a cylinder 135; a cylinder rod 151 made slidable back and forth in the cylinder 135; and the stepping motor 152 for moving the cylinder rod 151 back and forth.

Above the cylinder rod 151, there is arranged a screw bolt 141 which is threaded in its outer circumference. This screw bolt 141 is screwed in a screw nut 136, which is fixed on a frame 146 of the dispenser. A timing belt 139 trained between a pulley 140 mounted on the screw bolt 141 and the spindle of the stepping motor 152.

On the other hand, the exit end portion at the lower end of the cylinder 135 and the pipette nozzle 132 are connected to communicate with each other via an air vent passage 181. The pipette nozzle 132 is biased outward with respect to the frame 146 of the dispenser 131 by a spring 145.

In the dispenser 131, moreover, there are arranged: a lower limit sensor 138 for detecting the lower limit of the cylinder rod 151; an upper limit sensor 143 for detecting the upper limit of the cylinder rod 151; and a grounding sensor 137 for detecting the grounding of the pipette nozzle 132.

The dispensing action of the dispenser 131 thus constructed is controlled by a separate control unit for the dispenser.

In the controls, specifically, the control unit measures the change in the internal pressure of the pressure sensor 134 while a suction is continued by lowering the disposable tip 133 mounted on the pipette nozzle 132 of the dispenser 131, to thereby detect either the arrival of the tip at the liquid level or the clogging of the tip with respect to a preset threshold value. When a predetermined suction is detected, the control unit stops the suction and raises the dispenser 131.

In the dispenser thus far described, however, the pressure sensor for detecting the internal pressure of the pipette nozzle is located at a position remote from the nozzle. This positioning raises a problem that the pressure in the pipette nozzle cannot be precisely detected.

SUMMARY OF THE INVENTION

It is, therefore, an object of the present invention to provide such a dispenser for sucking/discharging a liquid to be measured, and that can detect the pressure in the pipette nozzle precisely.

In order to achieve the object of the invention, the dispenser according to the present invention has the following construction. In the following description: a vacuum refers to an air pressure lower than the atmospheric level; a rise in the vacuum refers to an air pressure falling toward atmospheric pressure; and a fall in the vacuum refers to an air pressure rising toward atmospheric pressure.

(1) A dispenser for sucking and discharging a liquid from a nozzle by slidably moving a piston in the inside of a syringe by a motor mounted in a frame, wherein a detection sensor for detecting the internal pressure of the inside of the syringe is integrally formed by connecting its air inlet directly to a through hole formed to extend to the inner face of the syringe.

(2) A dispenser according to (1) comprising control unit for controlling the suction and discharge of the liquid from the nozzle.

(3) A dispenser according to (1), wherein the syringe formed integrally with the detection sensor is made removable from the frame.

(4) A dispenser according to (1), wherein the motor is so mounted in the frame that its motor portion is kept out of contact with the frame.

(5) A dispenser according to (1) or (2), wherein the control unit has functions to stop the suction action, when the detection sensor detects an abrupt rise of vacuum while the liquid is being sucked by the nozzle, and to judge a clogging, when the vacuum detected by the detection sensor rises after lapse of a predetermined time period from the stop of the suction action, and an out-of-liquid condition when the vacuum lowers.

(6) A dispensing device comprises: a control unit for controlling the suction and discharge of a liquid from a nozzle by slidably moving a piston in the inside of a syringe by a motor mounted in a frame; a dispenser including a detection sensor integrally formed by connecting its air inlet directly to a through hole formed to extend to the inner face of the syringe, for detecting the internal pressure in the syringe inside; a dispenser driver carrying a plurality of the dispensers for driving the same vertically or horizontally; and a plate arraying tube engaging holes in alignment longitudinally and transversely for engaging with tubes to be measured, wherein the pitch between the nozzle leading end of the nozzle unit of the dispenser and the nozzle leading end of the nozzle unit of the dispenser arranged adjacent to the former is equalized to the pitch between the tube engaging holes of the plate arranged in the transverse direction.

(7) A dispensing device according to (6), wherein the dispenser is given a structure, in which the syringe formed integrally with the detection sensor is made removable from the frame.

(8) A dispensing device according to (6), wherein the dispenser has the motor so mounted in the frame that its motor portion is kept out of contact with the frame.

(9) A dispensing device according to (6), wherein the control unit has functions to stop the suction action, when the detection sensor detects an abrupt rise of vacuum while the liquid is being sucked by the nozzle, and to judge a clogging, when the vacuum detected by the detection sensor rises after lapse of a predetermined time period from the stop of the suction action, and an out-of-liquid condition when the vacuum lowers.

Thus, the detecting ability of the sensor can be improved by opening the through hole for detecting the internal pressure in the syringe portion and by connecting the air inlet of the sensor directly to the through hole to thereby eliminate the pipeline to the sensor.

On the other hand, the nozzle unit is given the removable structure so that it can be exclusively replaced.

Moreover, the pitch of the nozzle leading ends and the pitch of the tube engaging holes of the plate are equalized so that the dispensing actions can be simultaneously performed in case a plurality of dispensers are arranged.

On the other hand, the clogging and the out-of-liquid condition during liquid suction are judged in the detecting state of the detection sensor so that the precise detection can be made without requiring any other component.

DETAILED DESCRIPTION OF PREFERRED EMBODIMENT

Embodiments of a dispenser and a dispensing device according to the invention will be described with reference to the accompanying drawings.

Figure 1:
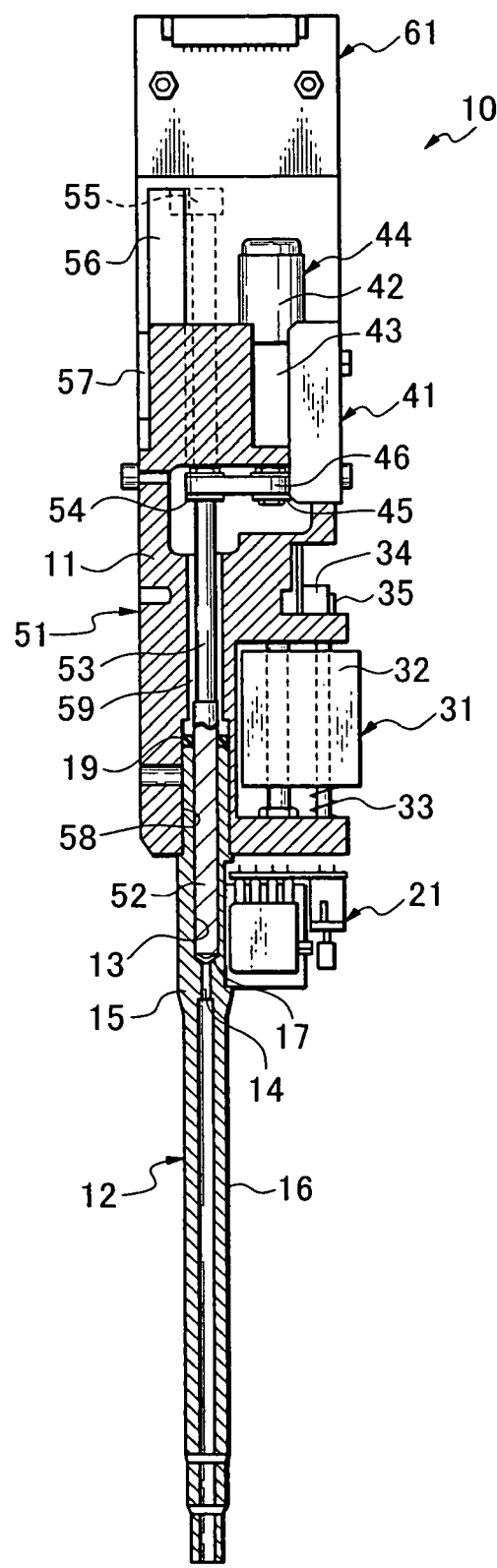
FIG. 1 is a side elevational view showing a dispenser according to the invention partially in section.
Figure 2:
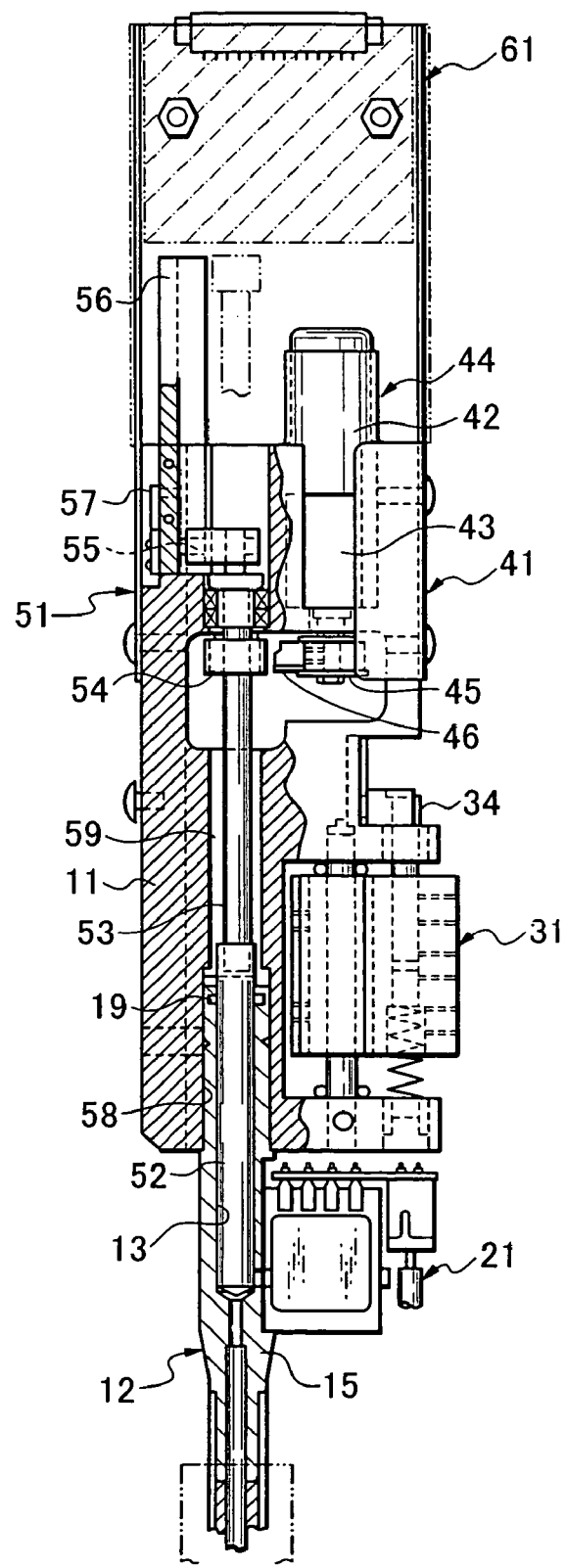
FIG. 2 is a partially enlarged section of the same.

As shown in FIG. 1 and FIG. 2, a dispenser 10 according to the invention is mounted on a frame 11, which is formed to have a slender shape. The dispenser 10 is substantially constructed to include: a nozzle unit 12 made removable for fitting a tip on its leading end; a sliding unit 51 for moving a piston 52 up and down in the direction of an axis, on which the nozzle unit 12 is mounted; a driving unit 41 having a stepping motor 44 for moving the piston 52 of the sliding unit 51 up and down; and a dispensation control unit 61 for controlling signals coming from sensors and the stepping motor 44.

Figure 3:
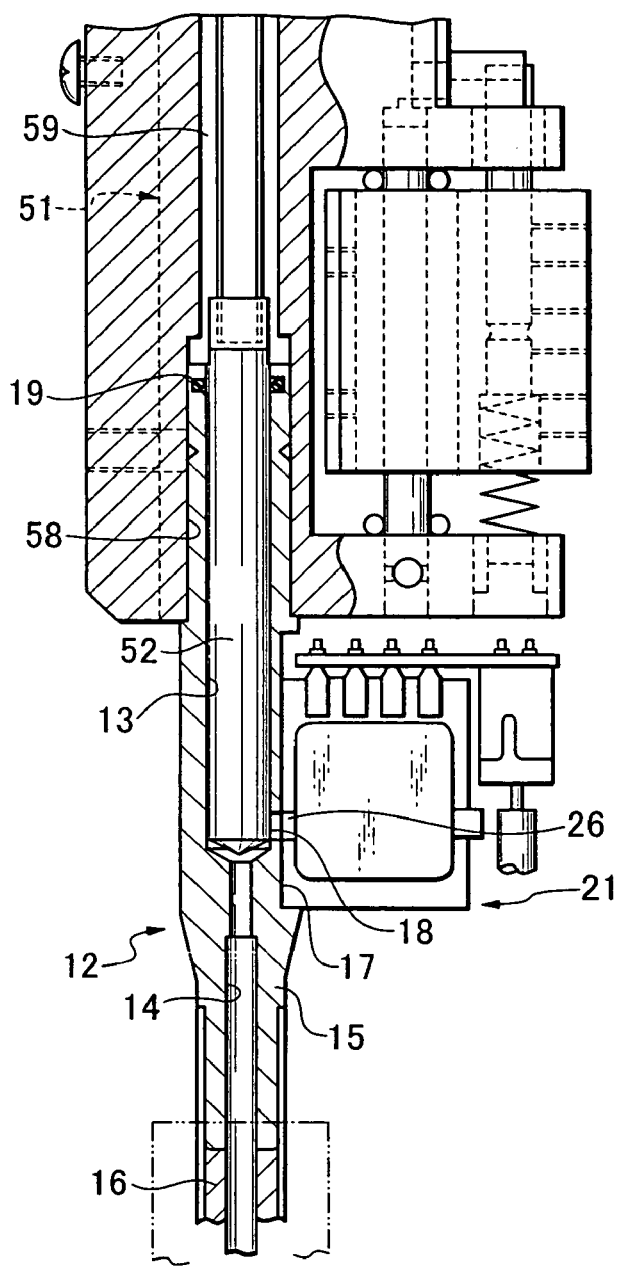
FIG. 3 is a partially sectional elevational side view of the same showing a nozzle unit on an enlarged scale.
Figure 4:
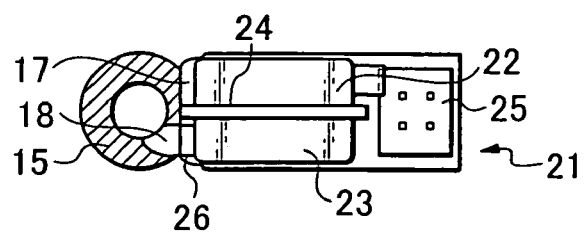
FIG. 4 is a top plan view of the nozzle unit of the same.

With specific reference to FIG. 3 and FIG. 4, the nozzle unit 12 is made hollow in its inside and is provided on its upper side with a piston engaging bore 13 sized to allow the piston 52 to move up and down. The nozzle unit 12 is constructed of: a syringe 15, which is provided with a vent hole 14 communicating with the piston engaging bore 13 and having about one half diameter of that of the piston engaging bore 13; and a pipette nozzle 16 having an internal diameter equal to that of the syringe 15 and an external diameter smaller than that of the same. The nozzle unit 12 further includes a pressure sensor mounting portion 17 on its outer side and at the portion of the syringe 15. The pressure sensor mounting portion 17 is made to have a structure capable of receiving the pressure of the inside of the syringe 15 directly, by notching the outer circumference of the portion, on which the piston 52 grounds, by forming a through hole 18 extending through the grounding portion of the syringe 15, and by connecting an air inlet 26 of a second sensor 23 of a pressure sensor 21, directly to that through hole 18.

On the other hand, the structure is provided with a packing 19 on the inner circumference of the upper portion of the piston engaging bore 13.

The nozzle unit 12 having this structure is removably mounted in the sliding unit 51. When the nozzle unit 12 is mounted in the sliding unit 51, the leading end of the nozzle unit 12 is inserted into a nozzle engaging hole 58, and the piston 52 is inserted into the piston engaging bore 13. This mounting operation is completed by supporting the inserted piston 52 on the packing 19. The mounting state can be fixed by means of a not-shown screw while the outer circumference of the nozzle unit 12 and the inner circumference of the nozzle engaging hole 58 are in frictional engagement.

The pressure sensor 21 is constructed to include: a first sensor 22 for receiving the pressure of the atmosphere; the second sensor 23 for receiving the pressure of an object; a pressure detecting board 24 connecting the back portions of these first and second sensors 22 and 23 for detecting the pressures; and a connector for transmitting pressure signals detected by the pressure detecting board 24, to the outside. Thus, the pressure sensor has the structure, in which the sensors for detecting the pressures and the board for converting the pressures of the sensors into electric signals are integrally formed.

As shown in FIG. 1, a dispenser mounting unit 31 is constructed to move the dispenser 10 up and down as a whole and to have a sensor for detecting that the leading end of the nozzle unit 12 abuts against the object. The dispenser mounting unit 31 is constructed to include: a mount 32 guided in two axes; a spring 33 biasing the mount 32 upward at all times; and a dispensation abutment sensor 34 acting as a photo sensor for detecting that it is shielded or opened by a guide 35 mounted on the mount 32.

This mount 32 is attached to a not-shown driving member to thereby assemble the dispenser 10. Then, the dispenser 10 assembled is lowered toward a liquid to be measured. When the leading end of the nozzle unit 12 abuts against the liquid, the dispenser 10 itself ascends against the spring 33. As a result, the guide 35 disposed above the mount 32 is demounted from the photo sensor so that the dispensation abutment sensor 34 is turned ON to detect that the leading end of the nozzle unit 12 has contacted an abutment when the dispenser 10 descends.

As shown in FIG. 1 and FIG. 2, the driving unit 41 is arranged at an upper position of the frame 11. The driving unit 41 is composed of: the stepping motor 44 having a motor portion 42 kept out of contact with the frame 11 and a gear portion 43 engaging with the frame 11; a first pulley 45 fixed on the spindle of the stepping motor 44; and a timing belt 46 carried on the first pulley 45.

Thus, the motor portion 42 is kept out of contact with the frame 11 so that the heat to be generated by the motor portion 42 cannot or can hardly be conducted to the frame 11 to thereby avoid measurement error due to the thermal expansion.

As shown in FIG. 1 and FIG. 2, the sliding unit 51 is provided with the nozzle engaging hole 58 formed in a vertical direction for mounting the nozzle unit 12 therein, and a screwed communication hole 59 formed to communicate with the nozzle engaging hole 58. The sliding unit 51 is juxtaposed at a predetermined spacing to the driving unit 41 and is substantially constructed to include: the piston 52 formed into a predetermined cylindrical shape; a feed screw 53 connected to the piston 52 and having a screw-threaded outer circumference; a second pulley 54 screwed on the feed screw 53; a sensor dog 55 provided at the leading end of the feed screw 53 for acting as a guide; a dog guide 56 for guiding the sensor dog 55 in the vertical direction; and a piston lower limit sensor 57 for detecting the sensor dog 55 thereby to detect that the piston 52 is at the lower limit position. The timing belt 46 is carried on the second pulley 54 and the first pulley 45 of the driving unit 41.

In this sliding unit 51, the rotary motion of the stepping motor 44 of the driving unit 41 rotates the second pulley 54 through the timing belt 46. Then, the feed screw 53 screwed in the second pulley 54 moves upward and downward so that the piston 52 attached to the leading end of the feed screw 53 accordingly slides upward or downward.

As shown in FIG. 1 and FIG. 2, the dispensation control unit 61 controls the feed of a drive current to the stepping motor 44, and is constructed to include a circuit board for controlling the dispensing actions by receiving the signals from the piston lower limit sensor 57 of the sliding unit 51, the dispensation abutment sensor 34 of the dispenser mounting unit 31, and the pressure sensor 21 of the nozzle unit 12.

Figure 5:
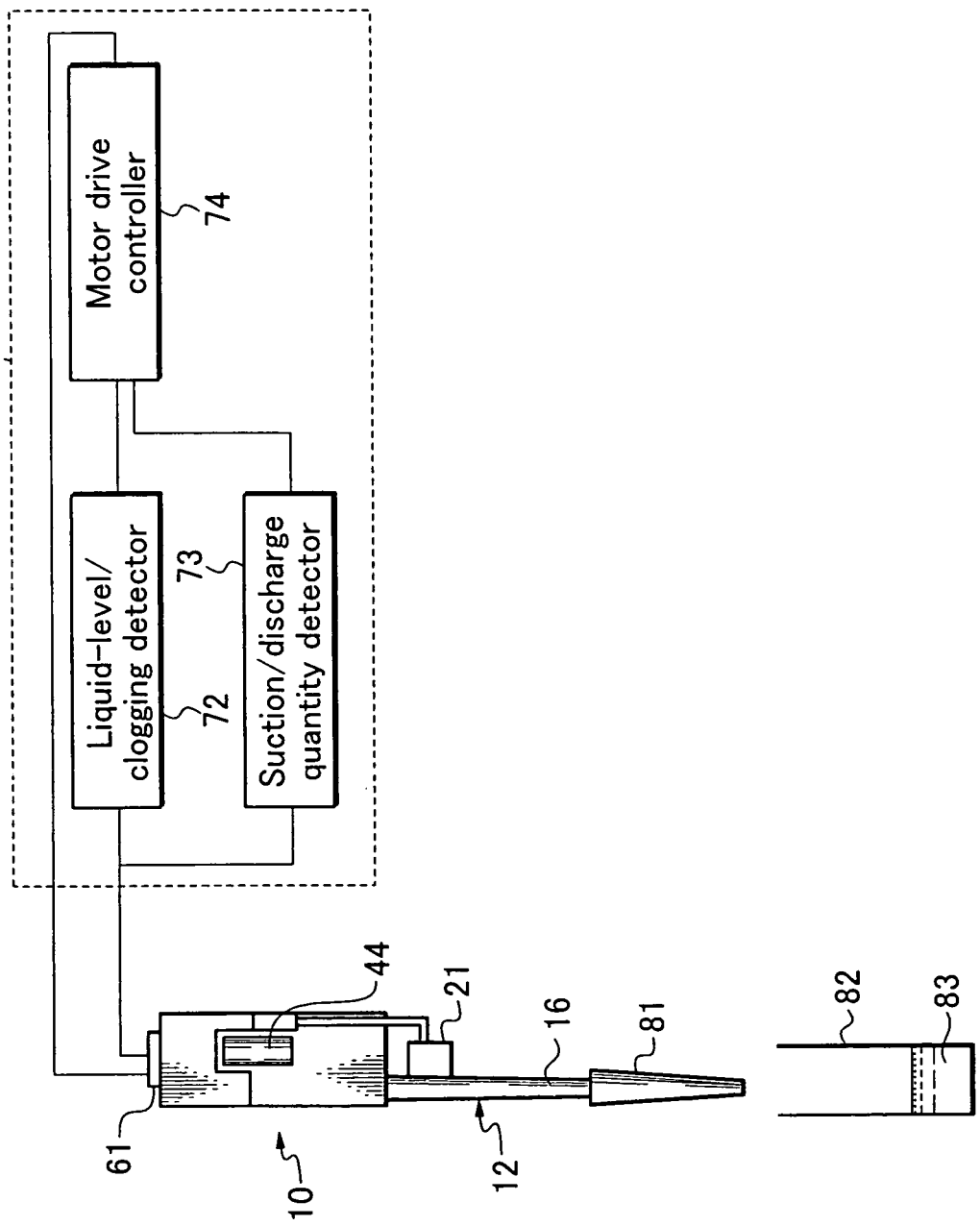
FIG. 5 is an explanatory diagram showing a dispensing device schematically.

The dispenser 10 thus constructed controls the dispensing actions with a control unit disposed outside thereof. As shown in FIG. 5, this control unit 71 is electrically connected with the dispensation control unit 61 of the dispenser. The control unit 71 is substantially constructed to include: a liquid-level/clogging detector 72 for detecting the arrival at the liquid level or the clogging with reference to a preset threshold hold by lowering a tip 81 fitted on the pipette nozzle 16 of the dispenser 10 and by measuring the change in the internal pressure of the pressure sensor 21 during a continuous sucking action; a suction/discharge quantity detector 73 for detecting the pressure change in the pressure sensor 21 to thereby detect the quantity of the sucked liquid and the discharge of the liquid; and a motor drive controller 74 for controlling the turning motion of the stepping motor 44 on the basis of the signals from the liquid-level/clogging detector 72 and the suction/discharge quantity detector 73.

Figure 6:
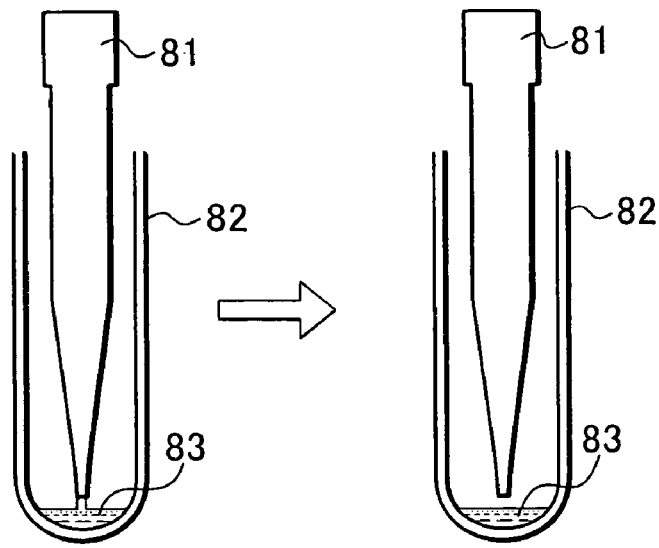
FIG. 6 is an explanatory view showing an out-of-liquid state of a tip attached to a nozzle.

The phenomena of the out-of-liquid state and the clogging state are described in the following. In the out-of-liquid case, as shown in FIG. 6, while the liquid is being sucked, its level lowers, and the liquid at the leading end of the tip 81 is pulled by the force, which is caused to return the liquid to the initial position by the surface tension, so that the liquid is torn off. In the internal pressure, the vacuum once rises abruptly and then lowers.

Figure 7:
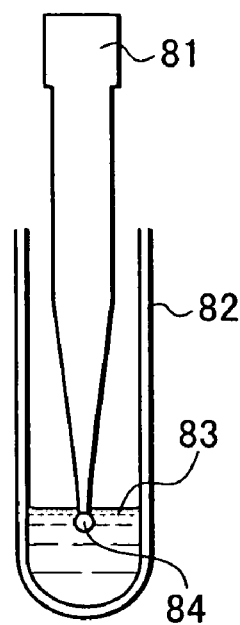
FIG. 7 is an explanatory view showing a clogging state of the tip attached to the nozzle.

In the clogging case, as shown in FIG. 7, if the leading end portion of the tip 81 sucks a foreign substance during the sucking action, the vacuum also abruptly rises, and this vacuum rise continues thereafter.

When the out-of-liquid state or the clogging thus occurs, the vacuum rises instantly, and then lowers in the out-of-liquid case, but the vacuum rise continues in the clogging case. Therefore, this vacuum is detected to judge the clogging if the vacuum rise and then continues, and the out-of-liquid state if the vacuum then lowers after rising.

The description is provided especially for the out-of-liquid and the clogging conditions in the dispenser thus controlled by the control unit 71. These detections are made by lowering the dispenser 10 itself and by detecting it in terms of the pressure change of the pressure sensor 21 that the tip 81 has been immersed in the liquid level of a liquid 83 in a tube 82 to be measured.

Figure 8:
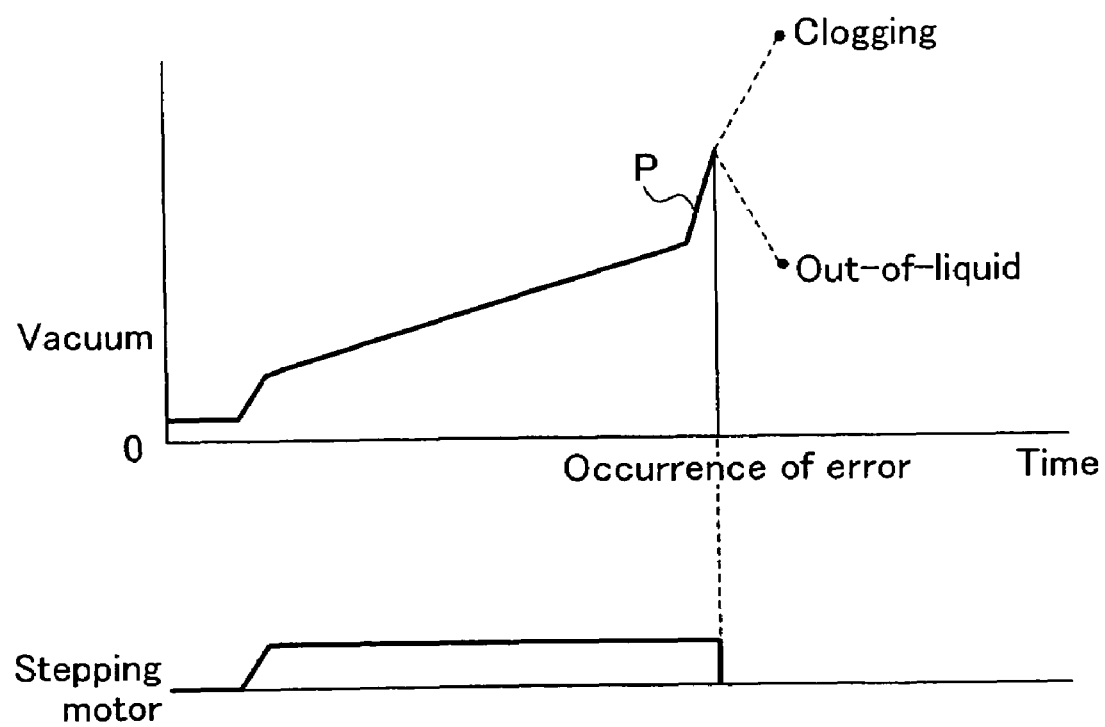
FIG. 8 is an explanatory diagram showing the out-of-liquid and clogging states.

Next, the sucking action is done, and the pressure is detected. The error is judged when an abrupt vacuum rise (as indicated at P) occurs as shown in FIG. 8, and the feed of the drive current to the stepping motor 44 is interrupted to stop the motion of the piston 52.

After lapse of a predetermined time period, the pressure in the syringe 15 is measured by the pressure sensor 21.

The out-of-liquid state is judged if the vacuum is lower than that at the time when the pressure in the syringe 15 is judged as an error, and the clogging is judged if the vacuum rises instead.

The dispensing device will be described in the following.

Figure 9:
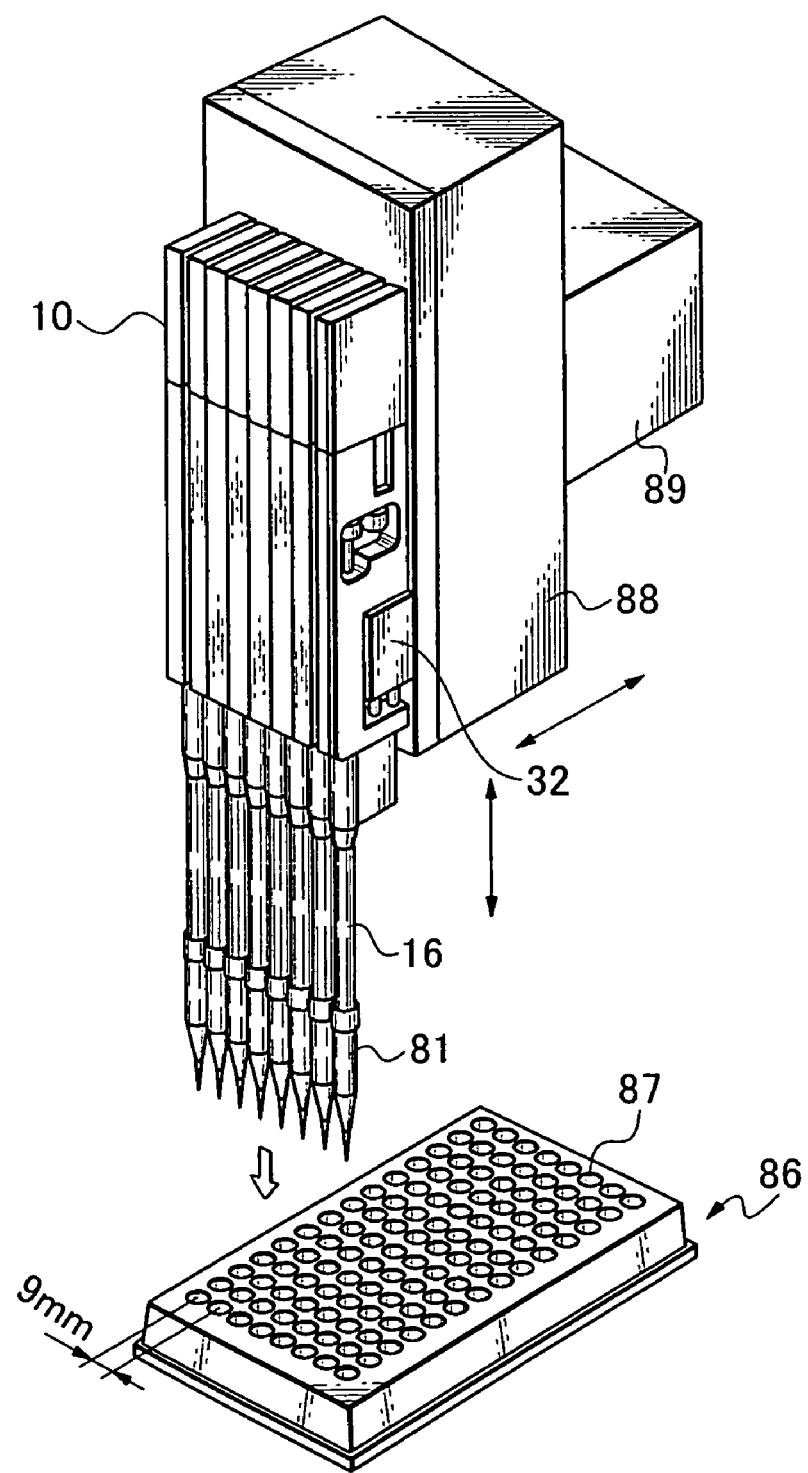
FIG. 9 is a perspective view showing the dispensing device schematically.
Figure 10:
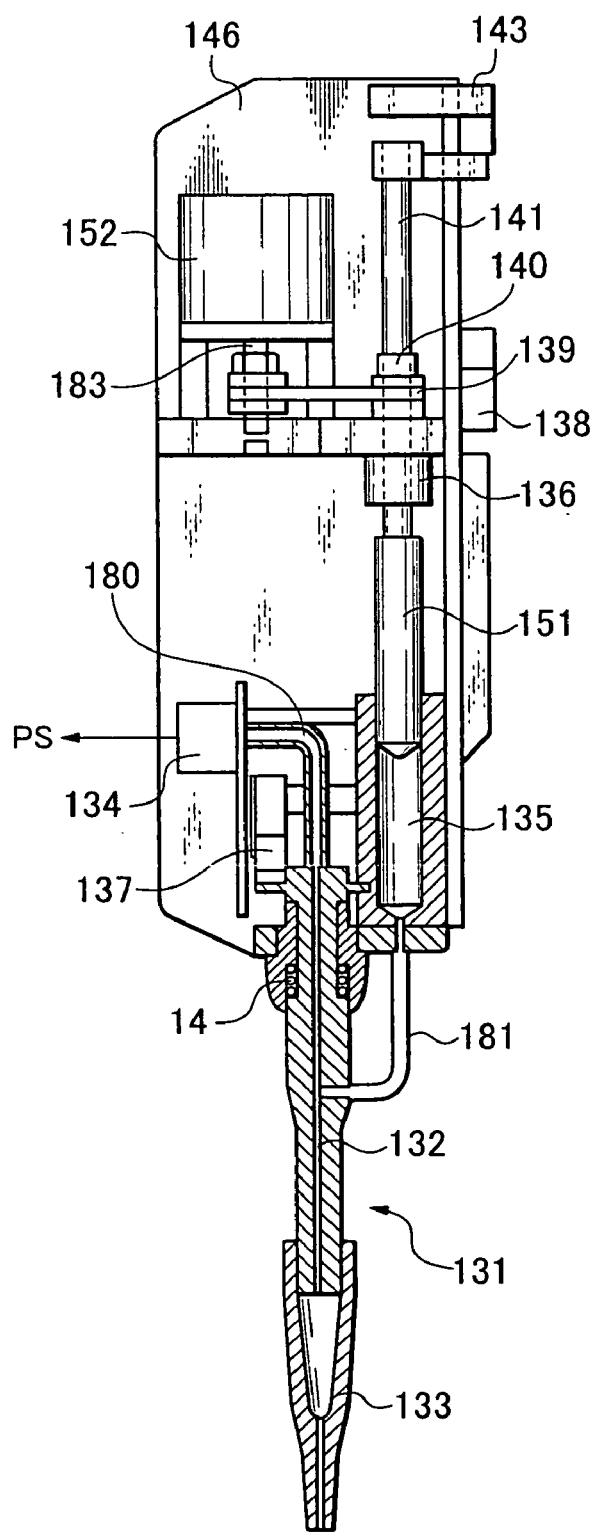
FIG. 10 is a top plan view of a conventional dispenser in partial section.

As shown in FIG. 9, the dispensing device is constructed to include: a vertical driver 88 carrying the dispenser 10 for moving the carried dispenser 10 vertically; a horizontal driver 89 for moving the dispenser 10 carried on the vertical driver 88, in a horizontal direction; and a micro-plate 86 juxtaposing a plurality of tubes to be measured. The vertical driver 88 and the horizontal driver 89 together constitute a dispenser driver.

The vertical driver 88 is so constructed by arraying a plurality of the aforementioned dispensers 10, e.g., eight dispensers 10 in the case of the embodiment in one row that the spacing (e.g., 9 mm in the embodiment) between the pipette nozzles 16 of the dispensers 10 may be equal to that (e.g., 9 mm in the embodiment) between tube engaging holes 87 formed in the micro-plate 86. The eight dispensers 10 have their mounts 32 attached to the vertical driver 88.

The micro-plate 86 is provided with a plurality of tube engaging holes 87 for placing the tubes to be measured, and is constructed in the case of the embodiment by aligning eight transverse and fourteen longitudinal tube engaging holes 87, which total one hundred and twelve tube engaging holes 87 transversely and longitudinally. The spacing (or pitch) between the tube engaging holes 87 in one row is 9 mm, which is equal to the spacing (or pitch) between the pipette nozzle 16 of the dispenser 10 and the pipette nozzle 16 of the adjoining dispenser 10. In case the number of the dispensers 10 is eight for the eight tube engaging holes 87 in one transverse row, the dispensing device can dispense one row simultaneously.

In the dispensing device thus constructed, the vertical driver 88 moves downward to insert the tips 81 of the eight dispensers 10 into the measured tubes placed in the tube engaging holes 87 so that the dispensing actions (for the suctions or discharges) are performed. Next, the vertical driver 88 moves upward to raise the tips 81 of the eight dispensers 10 away from the measured tubes to the positions shown in FIG. 9. After this, the horizontal driver 89 moves all the dispensers 10 in the horizontal direction, i.e., rightward of the location shown in FIG. 9 so that the dispensing occurs for the measured tubes of the next row. Thus, one row of the micro-plate 86 can be simultaneously dispensed by the dispensers 10 so that the dispensing actions achieved can be efficient.

As has been described hereinbefore, the dispenser according to the invention has the pressure sensor integrated with the syringe and enjoys advantages that it can eliminate the error of the measured pressure, which might otherwise be caused due to a dynamic distortion by the pipeline, and that it can drastically improve the response to the change in the internal pressure to be measured.

On the other hand, the nozzle unit having the pressure sensor integrated with the syringe is made removable. Therefore, the dispenser enjoys an advantage that the nozzle itself can be simply replaced to drastically reduce the time period for the maintenance and the replacing work.

Moreover, the motor portion of the stepping motor is kept out of contact with the frame so that the heat produced from the motor is not or hardly conducted to the frame. Therefore, the dispenser enjoys an advantage that it can avoid the measurement error, which might otherwise be caused by the thermal expansion.

Furthermore, the pitch between the tube engaging holes of the plate and the pitch between the nozzles of the dispensers are equalized to provide another advantage that the dispensing actions can be simultaneously performed by a plurality of dispensers.

What is claimed is:

1. A dispensing device comprising:
    a plurality of dispensers, each of the dispensers including a nozzle unit comprising a syringe, and a detection sensor integrally formed by connecting its air inlet directly to a through hole formed to extend to the inner face of the syringe, for detecting the internal pressure in the syringe inside;
    a dispenser driver carrying the dispensers for driving the dispensers vertically or horizontally; and
    a plate having an array of tube engaging holes in alignment longitudinally and transversely for engaging with tubes to be measured,
    wherein the pitch between a nozzle leading end of the nozzle unit of a first one of the dispensers and a nozzle leading end of the nozzle unit of a second one of the dispensers arranged adjacent to the first one of the dispensers is equalized to the pitch between the tube engaging holes of the plate arranged in the transverse direction; and
    a control unit configured to control the suction and discharge of liquid from the nozzle units by slidably moving pistons in the inside of the syringes by motors mounted in frames, respectively.

2. A dispensing device according to claim 1, wherein, for each of said dispensers, said dispenser is given has a structure, in which the syringe is formed integrally with the detection sensor and is made removable from the frame.

3. A dispensing device according to claim 1, wherein, for each of said dispensers, said dispenser has the motor so mounted in the frame that a motor portion of the motor is kept out of contact with the frame.

4. A dispensing device according to claim 1, wherein said control unit has functions to stop the suction action, when the detection sensor of one of the dispensers detects an abrupt rise of vacuum while the liquid is being sucked by the nozzle unit, and to judge a clogging, when the vacuum detected by the detection sensor rises after lapse of a predetermined time period from the stop of the suction action, and an out-of-liquid state when the vacuum lowers.

\* \* \* \* \*